(12) United States Patent
Aflatoon

(10) Patent No.: US 9,204,907 B2
(45) Date of Patent: Dec. 8, 2015

(54) DYNAMIC INTER-SPINOUS PROCESS SPACER

(71) Applicant: Kamran Aflatoon, Corona del Mar, CA (US)

(72) Inventor: Kamran Aflatoon, Corona del Mar, CA (US)

(*) Notice: Subject to any disclaimer, the term of this patent is extended or adjusted under 35 U.S.C. 154(b) by 0 days.

(21) Appl. No.: 14/255,337

(22) Filed: Apr. 17, 2014

(65) Prior Publication Data

US 2014/0228886 A1 Aug. 14, 2014

Related U.S. Application Data

(63) Continuation-in-part of application No. 13/184,150, filed on Jul. 15, 2011, now Pat. No. 8,790,373.

(51) Int. Cl.
*A61B 17/70* (2006.01)
*A61B 17/00* (2006.01)

(52) U.S. Cl.
CPC ......... *A61B 17/7067* (2013.01); *A61B 17/7065* (2013.01); *A61B 17/7068* (2013.01); *A61B 2017/00557* (2013.01)

(58) Field of Classification Search
CPC ......... A61F 2/44; A61F 2/4405; A61F 2/441; A61B 17/7062; A61B 17/7065; A61B 17/7067
See application file for complete search history.

(56) References Cited

U.S. PATENT DOCUMENTS

| 2005/0203624 | A1* | 9/2005 | Serhan et al. | 623/17.11 |
|---|---|---|---|---|
| 2006/0004447 | A1* | 1/2006 | Mastrorio et al. | 623/17.11 |
| 2007/0106385 | A1* | 5/2007 | Zucherman et al. | 623/17.13 |
| 2007/0233076 | A1* | 10/2007 | Trieu | 606/61 |
| 2007/0270823 | A1* | 11/2007 | Trieu et al. | 606/61 |
| 2009/0216274 | A1* | 8/2009 | Morancy-Meister et al. | 606/247 |
| 2010/0106190 | A1* | 4/2010 | Linares | 606/249 |
| 2011/0295370 | A1* | 12/2011 | Suh et al. | 623/17.12 |
| 2011/0295373 | A1* | 12/2011 | Foley et al. | 623/17.16 |

* cited by examiner

*Primary Examiner* — Eduardo C Robert
*Assistant Examiner* — Julianna N Harvey
(74) *Attorney, Agent, or Firm* — Ober, Kaler, Grimes & Shriver; Royal W. Craig

(57) ABSTRACT

An interspinous process spacer for distraction of the vertebra including a body portion having an operative panel for increasing the height thereof and defining an internal void in which an expandable member is provided for actuating the operative panel. A self sealing percutaneous access port is provided to enlarge the expandable member and actuate the operative panel. The body portion is anchored by flanges secured to adjacent spinous process. The port allows for adding or removing fluid from the one or more chambers or envelopes of the expandable member in order to adjust the height of the body and thus the interspinous process spacing. Subsequent to initial implantation and expansion the volume of the expandable member may be increased or decreased in a non-surgical in-office procedure in which a needle is used to add or remove fluid from the expandable member via the port and tubular member.

15 Claims, 12 Drawing Sheets

DYNAMIC INTER-SPINOUS PROCESS SPACER

CROSS-REFERENCE TO RELATED APPLICATIONS

The present application is a continuation in part of U.S. patent application Ser. No. 13/184,150 filed Jul. 15, 2011 which is incorporated herein by reference and which claims priority from provisional application 61/364,473 filed Jul. 15, 2010 which is also incorporated herein by reference.

BACKGROUND OF THE INVENTION

1. Field of the Invention

The present invention relates generally to devices and methods for treating spinal disorders and more specifically to a dynamic, variable height inter-spinous process spacer that can be implanted in a minimally invasive manner.

2. Description of the Background

Degeneration of the intervertebral discs and the concomitant instability and translocation of the vertebra (spondylolisthesis) is a common cause of back pain and may result from a variety of problems including congenital deformity, age related degeneration, osteoporosis, tumor and disc herniation as a result of trauma. Disc degeneration, for whatever reason, results in compression of the spinal nerve roots (stenosis) resulting in pain. Other causes of stenosis include changes in ligament morphology, vertebral bone spurs in or near the spinal canal and degeneration of the facet joints. Palliative care such as physical therapy, non-steroidal anti-inflammatories (NSAIDS) and epidural steroid injections are often successful used in the treatment of mild cases but more extreme or degenerative cases may require a surgical approach to stabilize the spine and relieve pressure.

The standard surgical treatments for symptomatic degenerative spondylolisthesis and spinal stenosis have, for many years, included decompressive laminectomy in which the lamina of one or more vertebrae is removed to enlarge the space available and relieve pressure on the spinal cord or spinal nerve roots. Lumbar decompression and spinal fusion to decompress the nerve roots and/or spinal cord and to stabilize the spine are also frequently employed. However, many patients suffering from degenerative conditions have comorbidities that make them less than perfect surgical candidates. As a result, several different methods have more recently been devised as alternative treatments for degenerative spondylolisthesis and spinal stenosis.

One such alternative treatment is inter-spinous process distraction (IPD) which is also known as interspinous distraction or posterior spinal distraction. During IPD the spinous processes are mechanically pushed apart or distracted to relieve pressure on the spinal cord and/or nerve roots that is caused by the spondylolisthesis and spinal stenosis. An inter-spinous process spacer may be inserted into and retained in the interspinous process space created by the procedure to maintain the modified geometry.

The overall goals of traditional lumbar decompression with or without lumbar fusion and IPD are the same in that they both aim to relieve lower extremity neuropathy and claudication and may alleviate low back pain. IPD, however, offers advantages over the standard treatment in that it is not as invasive as laminectony or lumbar decompression and spinal fusion leading to shorter surgery times and shorter hospital stays and rehabilitation periods. IPD can further be accomplished under local anesthesia, preserves more local bone and soft tissue, has a reduced risk of epidural scarring and cerebrospinal fluid leakage and is reversible so as not to limit any future treatment options. The potential complications of IPD include dislodgement of the spacer, incorrect positioning or sizing of the spacer, fracture of the spinous process, foreign body reaction to the spacer (e.g., allergic reaction to titanium alloy) and mechanical failure of the spacer.

It would, therefore, be an improvement in this art to provide an interspinous process spacer that can be implanted in a minimally invasive procedure so as to retain the advantages of existing methods but that avoids the limitations of previous spacers. Such a spacer would be capable of being securely retained in place, would maintain the greatest possible contact area with the spinous processes so as to distribute loading forces and reduce the chance of fracture, would be of a robust design that is unlikely to fail mechanically and constructed of materials that are unlikely to cause allergic reactions. Such a spacer would further be capable of being sized and positioned during the implantation procedure and of being resized by percutaneous methods after implantation for an extended or indefinite period.

SUMMARY OF THE INVENTION

Accordingly, there is provided an interspinous process spacer and method of implantation for distraction of the vertebra including an expandable member, a self sealing percutaneous access port in fluid engagement with the expandable member and an anchor member. The anchor member defines a void space between lateral members that contains the expandable member and can be inserted between the spinous process of adjacent vertebra. The anchor member includes one or more flanges to secure the spacer to at least one of the adjacent spinous processes by screws or similar mechanical fastener when the spacer is situated between the vertebrae. In alternate embodiments one or more of the flanges are removably secured to the anchor member through the operation of a bracket or brackets. One or more operative panels are movably and preferably pivotably positioned between the lateral members of the body so as to form an upper and/or lower surface of the anchor member, as the case may be. Inflation of the expandable member by introduction of a flowable material enlarges an end of the expandable member and causes the operative panels to pivot or move thereby increasing the height of the anchor members and thus the height of the space between the spinous processes.

The port allows for adding or removing fluid from the one or more chambers or envelopes of the expandable member in order to adjust the volume of the expandable member and thus the interspinous process spacing. Subsequent to initial implantation and expansion the volume of the expandable member may be increased or decreased in a non-surgical in-office procedure in which a needle is used to add or remove fluid from the expandable member via the port and tubular member. The flowable material/fluid may be a liquid such as saline, gel such as silicone, or a viscous polymer and may further remain in a liquid state or harden to a viscoelastic state with or without additional intervention.

The foregoing objects, features and attendant benefits of this invention will, in part, be pointed out with particularity and will become more readily appreciated as the same become better understood by reference to the following detailed description of a preferred embodiment and certain modifications thereof when taken in conjunction with the accompanying drawings.

DETAILED DESCRIPTION OF THE PREFERRED EMBODIMENTS

Figure 1:
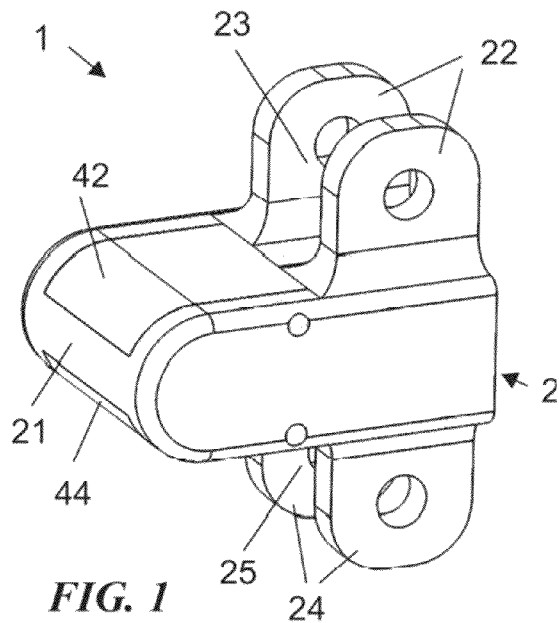
FIG. 1 is a perspective view of an interspinous process spacer according to the present invention with the movable panels in a stowed position.
Figure 2:
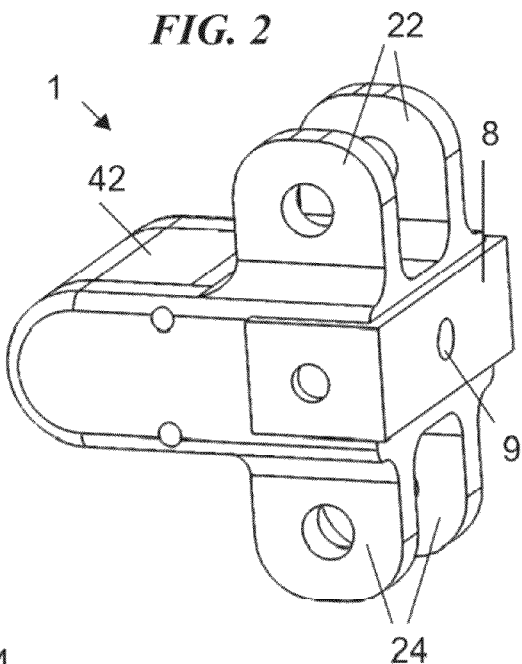
FIG. 2 is a perspective view of an interspinous process spacer according to the present invention with the end cap in place.
Figure 3:
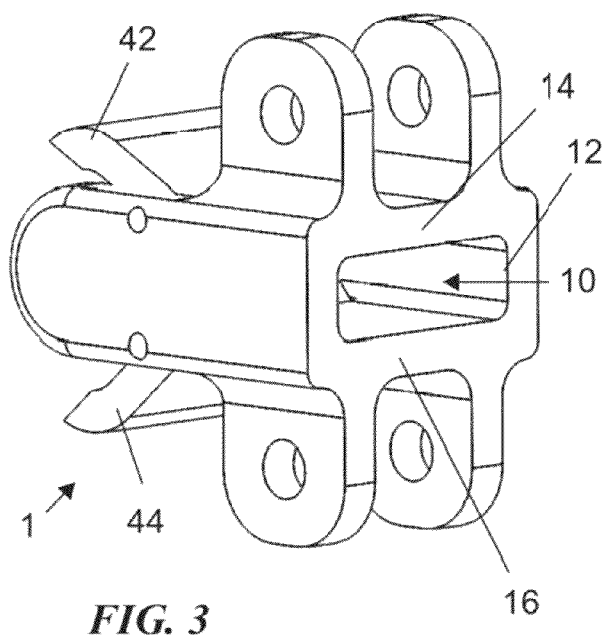
FIG. 3 is a perspective view of an interspinous process spacer according to the present invention with the movable panels in a deployed position.
Figure 4:
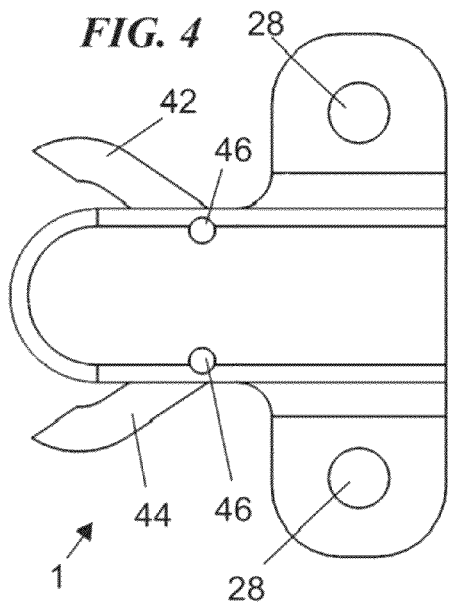
FIG. 4 is a side view (lateral sagittal plane) view of an interspinous process spacer according to the present invention with the movable panels in a deployed position.
Figure 5:
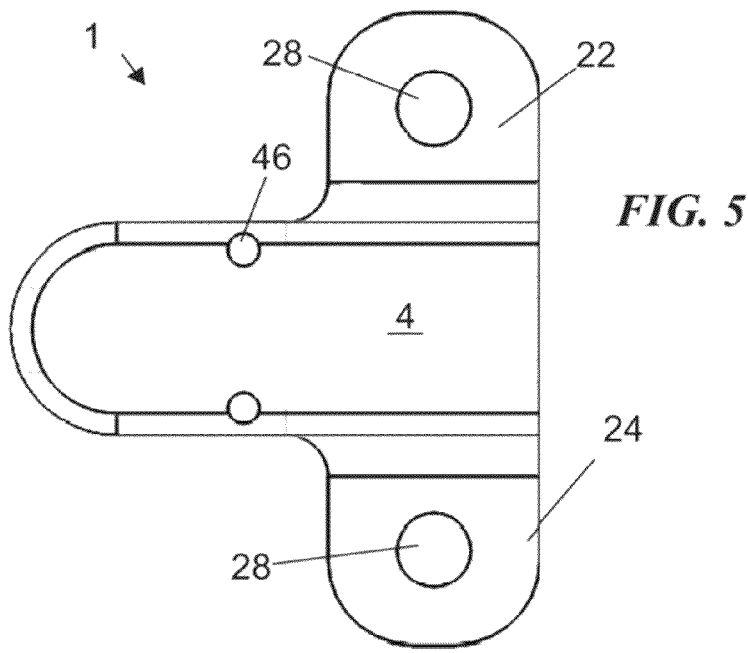
FIG. 5 is a lateral view of an interspinous process spacer according to the present invention with the movable panels in a stowed position.
Figure 7:
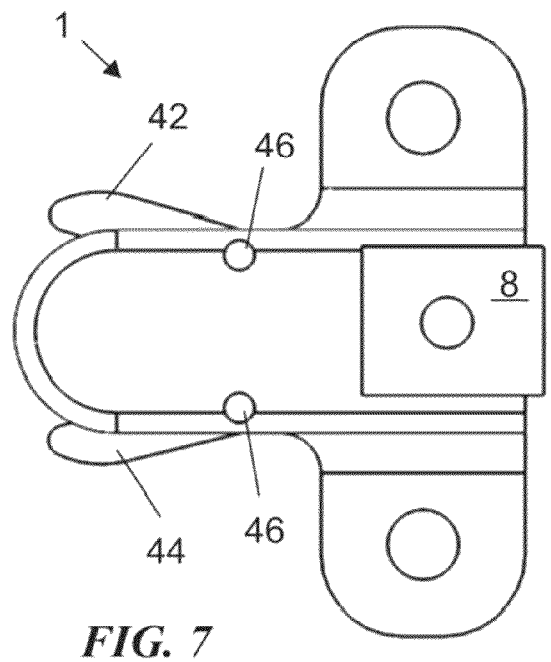
FIG. 7 is a lateral view of an interspinous process spacer according to the present invention with the movable panels in a deployed position.
Figure 6:
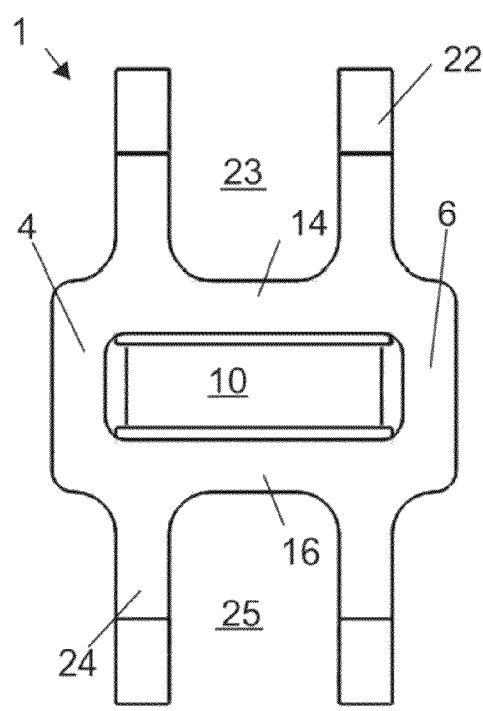
FIG. 6 is a posterior view of an interspinous process spacer according to the present invention.

With collective reference to FIGS. 1 through 9, an interspinous process spacer 1 having a body portion 2 is provided. In the depicted embodiment the body portion 2 is a generally elongate member defining an internal void 10 extending between lateral sides 4, 6 from an opening 12 at posterior end of the body. The internal void 10 and opening 12 are further defined by top and bottom elements 14, 16 extending between the lateral sides 4, 6 and together encircling the void 10. The height of the lateral sides 4, 6 and thus of body portion 2 is selected to be received between the interspinous processes of adjacent vertebra of the spine and may preferably be from 5 to 15 mm depending on their intended location of implantation along the spinal column.

Extending from each of the top and bottom of the body portion 2 are means for anchoring or securing the spacer 1 to the spinous processes of the adjacent vertebra when the body portion is situated in the inter-spinous process space between the vertebrae. Preferably, the means for anchoring the spacer 1 are provided in the form of cooperatively paired flanges 22, 24 extending away from the body portion 2 to define channels 23, 25 there between in which the spinous process of the superior or inferior vertebra may be received, as the case may be. A hole 28 may preferably provided through which a screw or through-bolt is inserted to secure the bone within the channel 23, 25. Alternately, holes 28 may be provided in the form of an elongate slot so as to permit some relative movement between the spacer and the bone when the screw is in place. One skilled in the art will understand that a single upper and single lower flange may be utilized to secure the spacer in place as might other means known.

An end cap 8 may preferably be supplied to be removeably secured to the body portion 2 to selectively close the opening 12 as will be described. One or more holes 9 may preferably be provided through the cap 8 to adjust the volume of the expandable/collapsible member 100 as will also be described.

The lateral sides 4, 6 extend from the posterior end of the device to a tapered or rounded anterior end where they are optionally but preferably joined by a bridging member 21. The bridging member 21 is cooperatively tapered or rounded to match the shape of the lateral sides to facilitate implantation between the adjacent spinous processes. Between the lateral sides 4, 6 at the posterior end of the body portion 2, upper and lower operative panels 42, 44 are provided. The operative panels 42, 44 are cooperatively shaped with the top and bottom elements 14, 16 to form a largely continuous surface and follow the taper or round-over of the body portion as described and depicted. The operative panels 42, 44 preferably engage the bridging member 21 at the anterior end of the device when the bridging member 21 is present.

Operative panels 42, 44 are preferably moveably received between the lateral sides 4, 6 of the body portion 2 in the depicted embodiment but may be otherwise situated, such as being positioned outside of (that is, on the top of or on the bottom of) the lateral sides so as to extend the full width of the body portion 2. In the depicted embodiment, each of the operative panels is pivotably mounted at or near its posterior end between the lateral sides 4, 6. In this way the operative panels are permitted to rotate as depicted in, for example, FIG. 4 or 7, with the anterior ends moving away from the bridging member 21 without the posterior ends substantially protruding into the void 10. The distal, anterior ends of each of the operative panels 42, 44 are provided with an inward projecting protrusion or ridge 51. Protruding ridge 51 may extend perpendicular to the plane of the operative panels but are preferably angled toward the bridging member 21 to facilitate but also limit deployment of the operative panels by engagement with the bridging member 21 when then panels are at their the maximum deployed position, as will be described. Rotation of the operative panels 42, 44 away from the body portion 2 increases the overall height of the body portion 2 and distracts the adjacent vertebra when positioned between the spinous processes. Pins 46 or similar means are provided to facilitate pivoting of the panels 42, 44.

Figure 22:
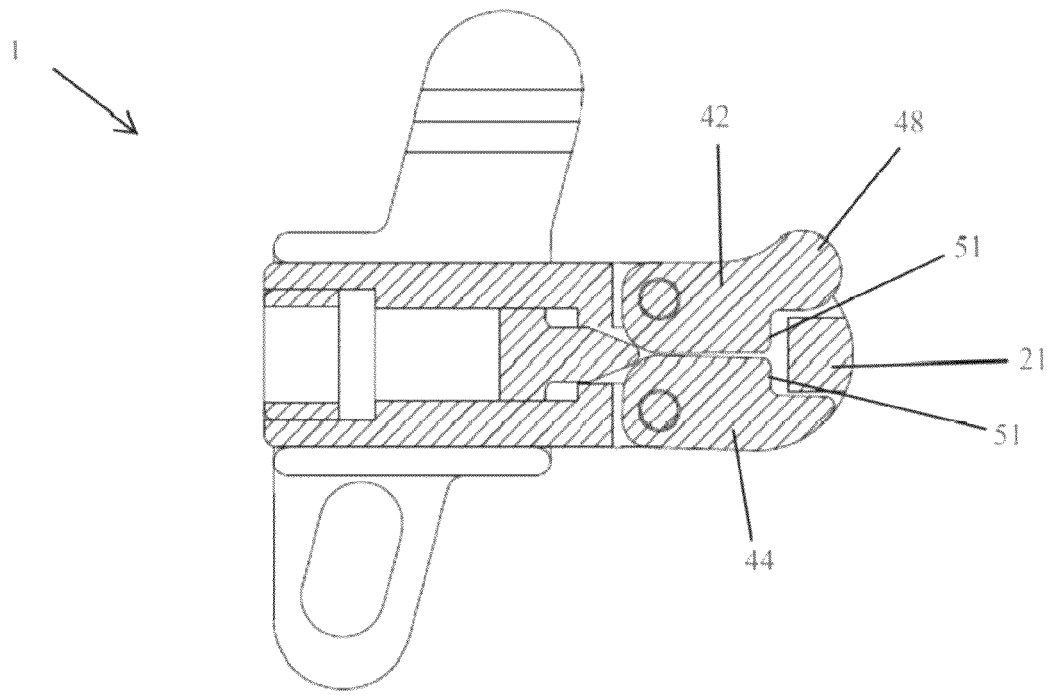
FIG. 22 is a section view of an alternative embodiment of an interspinous process spacer according to the present invention.
Figure 23:
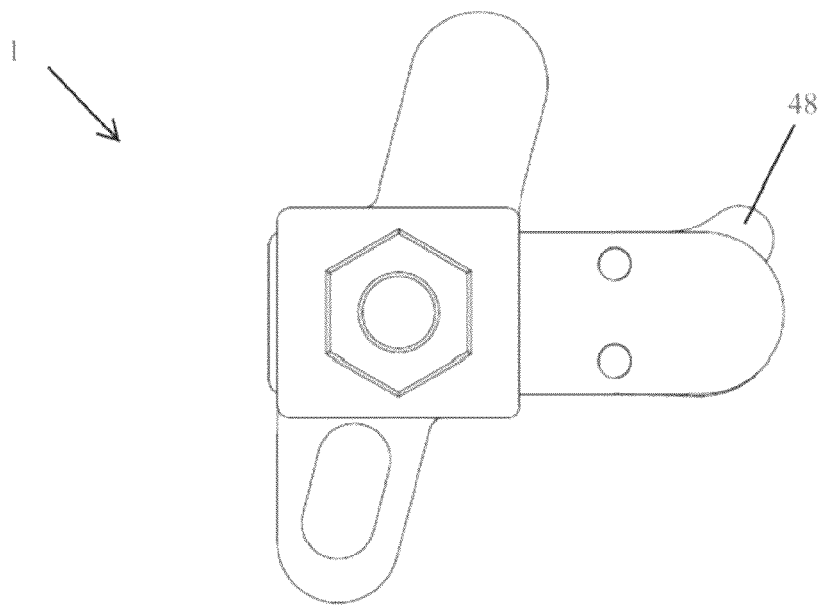
FIG. 23 is a side view of an alternate embodiment of an interspinous process spacer according to the present invention.
Figure 24:
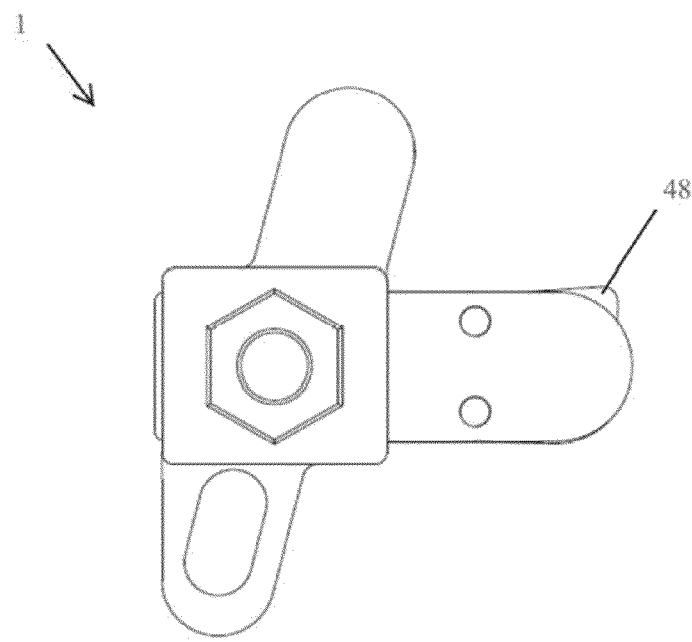
FIG. 24 is a side view of an alternate embodiment of an interspinous process spacer according to the present invention.

In preferred embodiments, the distal, anterior ends of one or both of the operative panels 42, 44 are also provided with a bulbous tip 48 to more closely engage the surface of the bone and provide additional distraction to adjacent vertebra. FIGS. 22 and 23 depict upper panel 42 having tip 48 extending upwards away from bridging member 21 and interior facing ridge 51 and interrupting the arcuate shape formed by the main body of spacer 1 so as to extend the height of the distal end of spacer 1 and provide a greater range of motion for panel 42. A further advantage of the addition of bulbous tip 48 onto the shape of panel 42 is that the rounded edge of tip 48 helps to prevent any scratching or chipping of the adjacent vertebra as panel 42 is rotated upwards or downwards, as will be described, after insertion of the spacer 1 into the interbody space. As shown in FIG. 24, bulbous tip 48 may alternatively take the shape of a squared-off protrusion that still sits above and interrupts the plane of the arcuate shape formed by the main body of spacer 1, while still supplying the advantages of additional distraction to adjacent vertebra and a greater range of motion for panel 42. The bulbous shaped tip 48 is shown in a closed position, prior to insertion, in FIGS. 22 and 23. In certain preferred embodiments (not shown), both upper and lower operative panels 42, 44 may be manufactured with bulbous tips 48 so as to provide an additional level of adjustability in the range of motion of the anterior end of spacer 1 and additional ease of movement of panels 42, 44 after insertion of the spacer into the interbody space.

Figure 8:
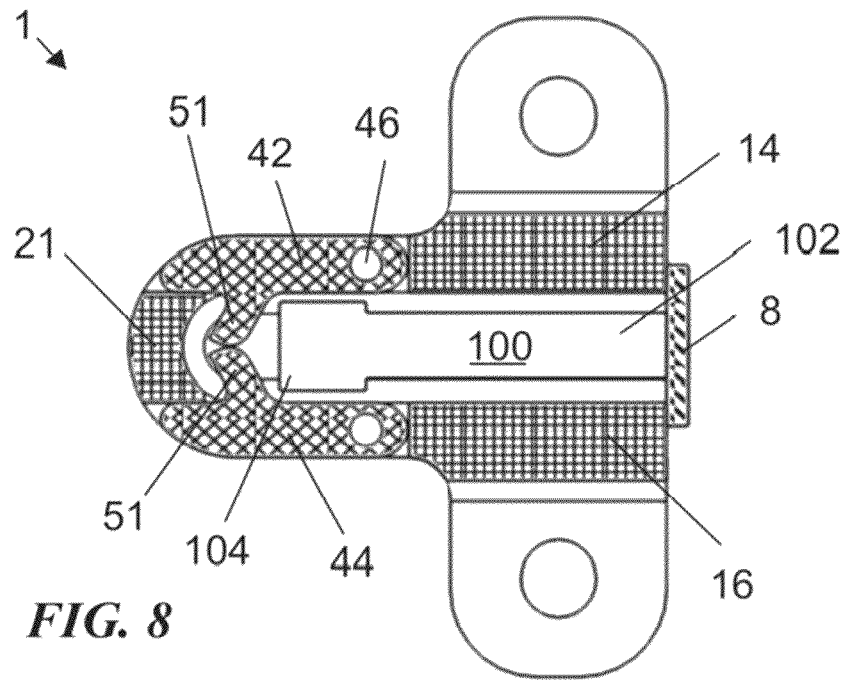
FIG. 8 is a lateral section view of an expandable collapsible member according to the present invention.
Figure 9:
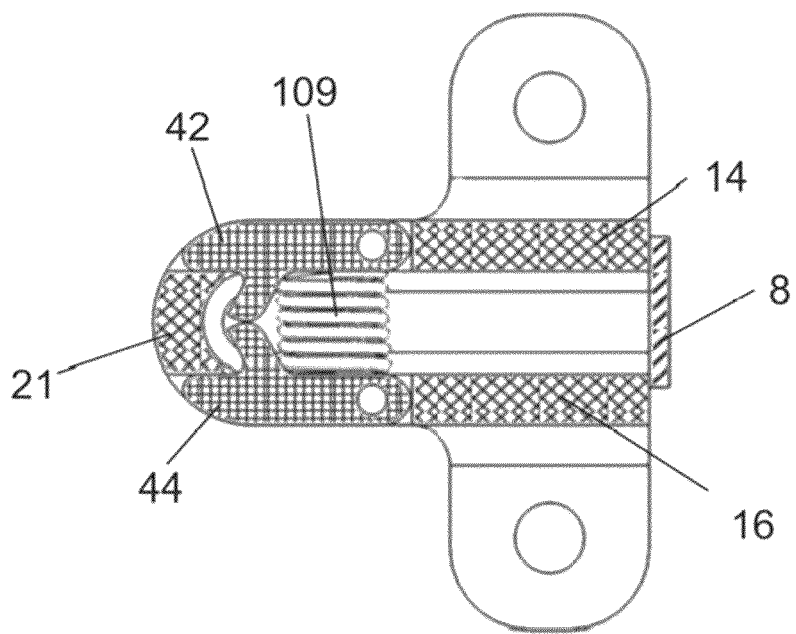
FIG. 9 is a lateral section view of an alternate embodiment of an expandable collapsible member according to the present invention.
Figure 10:
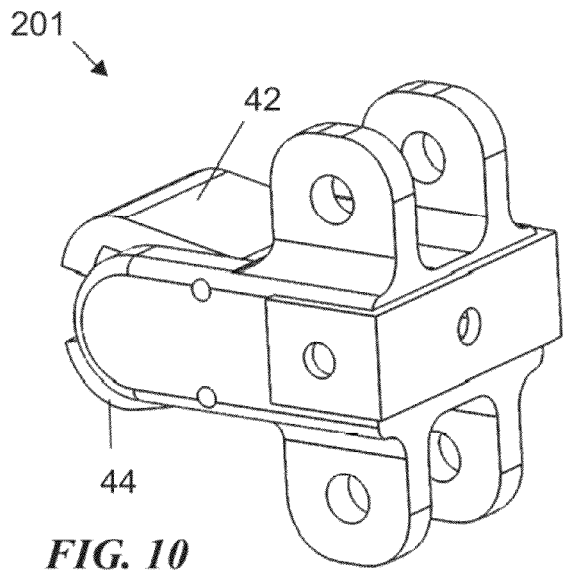
FIG. 10 is a perspective view of an alternate embodiment of an interspinous process spacer according to the present invention with the movable panels in a deployed position.
Figure 11:
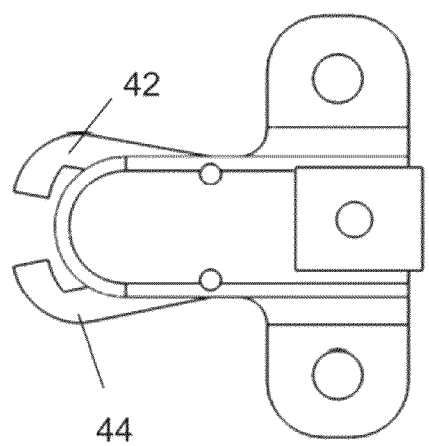
FIG. 11 is a side view of an alternate embodiment of an interspinous process spacer according to the present invention with the movable panels in a deployed position.
Figure 12:
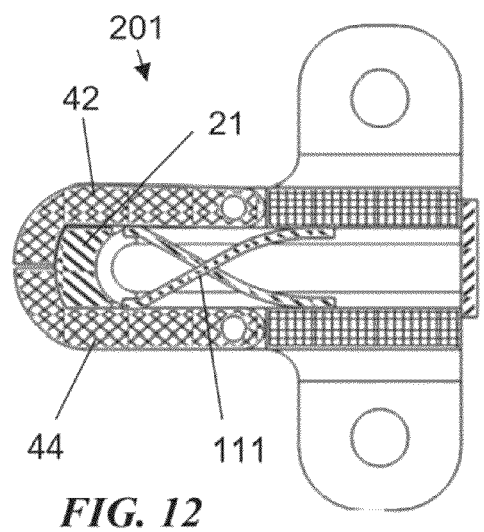
FIG. 12 is a section view of an alternate embodiment of an interspinous process spacer according to the present invention with the movable panels in a stowed position.

With reference to FIGS. 8 and 9, means for initiating rotation of the operative panels 42, 44 is provided within the void 10. In a preferred embodiment the means for initiation panel rotation is an expandable/collapsible member 100. The expandable/collapsible member 100 is preferably "T" shaped or otherwise shaped with a longitudinal portion 102 extending to a distal bulbous end region 104. In its initial, pre-implantation condition the expandable/collapsible member 100 is provided in a fully or partially evacuated state such that the longitudinal portion 102 is positioned within the void 10 with the collapsed end region 104 proximal to the bridging member 21 and to the ribs 51 of the operative panels 42, 44 in their stowed position. The expandable/collapsible member 100 may preferably be constructed of Kevlar, polypropylene, urethane, silicone elastomers such as polydimethylsiloxane or polymethylvinylsiloxane, polymethyl methacrylate, polycarbonate and copolymers thereof or other impermeable, implantable polymers as will be apparent to those skilled in the art.

Figure 18:
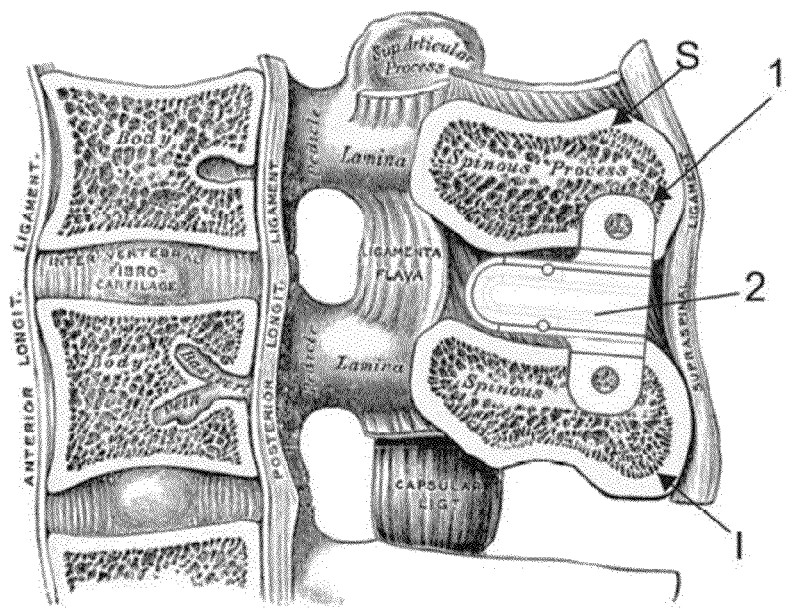
FIG. 18 is a schematic section view of an interspinous process spacer according to the present invention implanted but before deployment of the movable panels.
Figure 19:
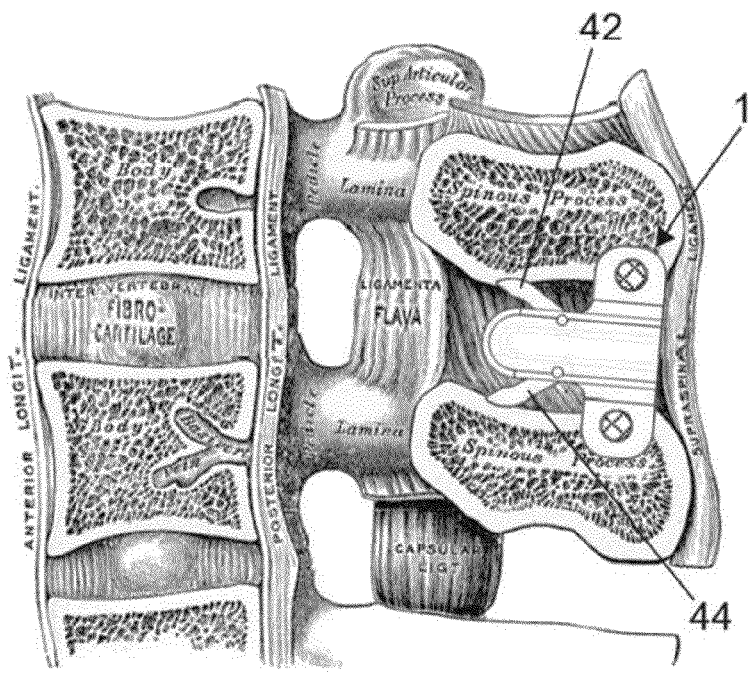
FIG. 19 is a schematic section view of an interspinous process spacer according to the present invention implanted after deployment of the movable panels.
Figure 20:
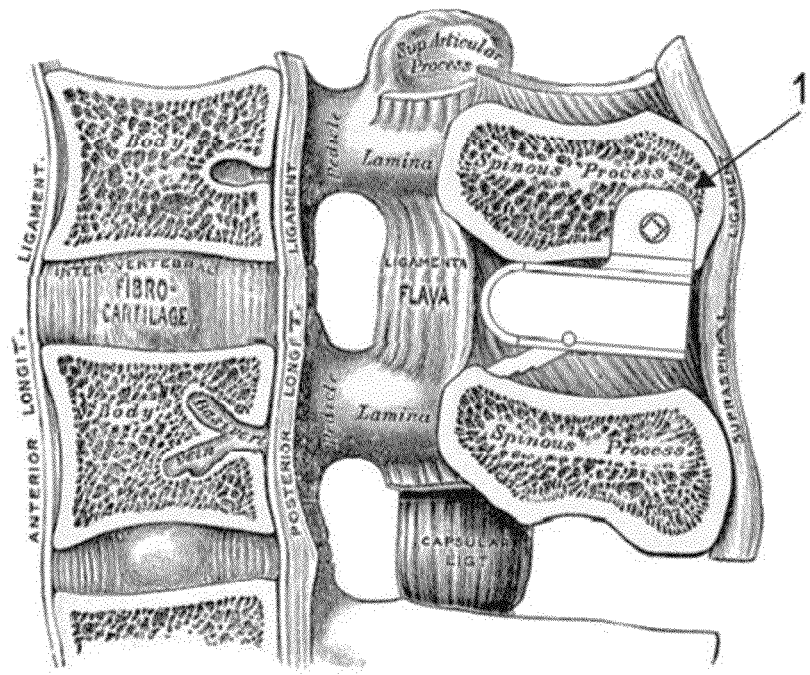
FIG. 20 is a schematic section view of an alternate embodiment of an interspinous process spacer according to the present invention implanted and after deployment of the movable panels.
Figure 21:
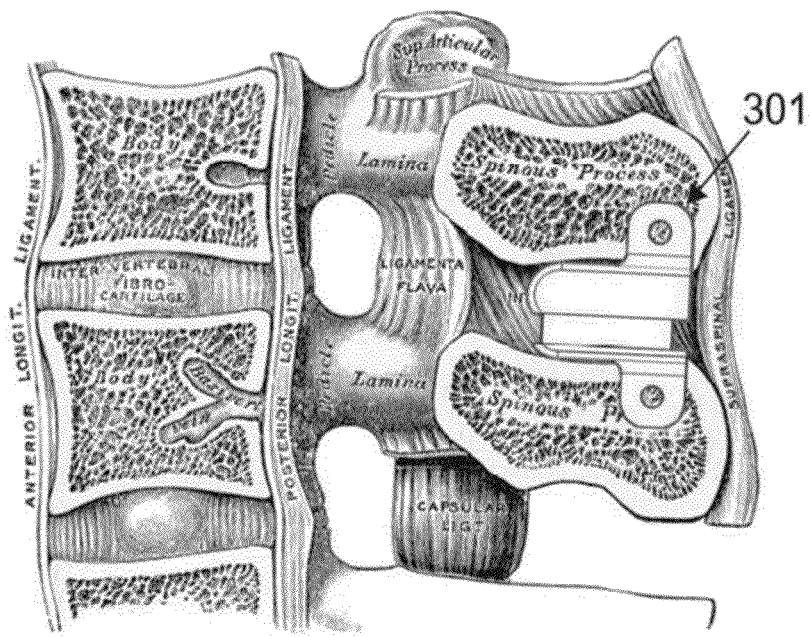
FIG. 21 is a schematic section view of an alternate embodiment of an interspinous process spacer according to the present invention implanted and after deployment.

With reference to FIGS. 18 and 19, in use the spacer 1 is implanted in a mini-open procedure in which the interspinous ligament is resected and the body portion 2 positioned within the interspinous space. The deflated expandable/collapsible member 100 is preferably secured in position prior to implantation and is most preferably inside the void 10 in a partially inflated state so as to generally fill the void and thereby be secured inside, but without actuating the operative panels 42, 44. The tapered or arcuate anterior end of the body portion 2 may provide an initial amount of distraction with direct contact to the superior (S) and inferior (I) spinous processes as it is worked into place. Alternately, an instrument may be applied to distract the vertebra and facilitate initial insertion of the spacer 1. When positioned to the surgeon's satisfaction, bone screws are driven through holes 30 in one of the pairs of flanges 22, 24 or both pairs of flanges if holes 30 are provided as elongate slots to secure the spacer 1 in position.

Figure 25:
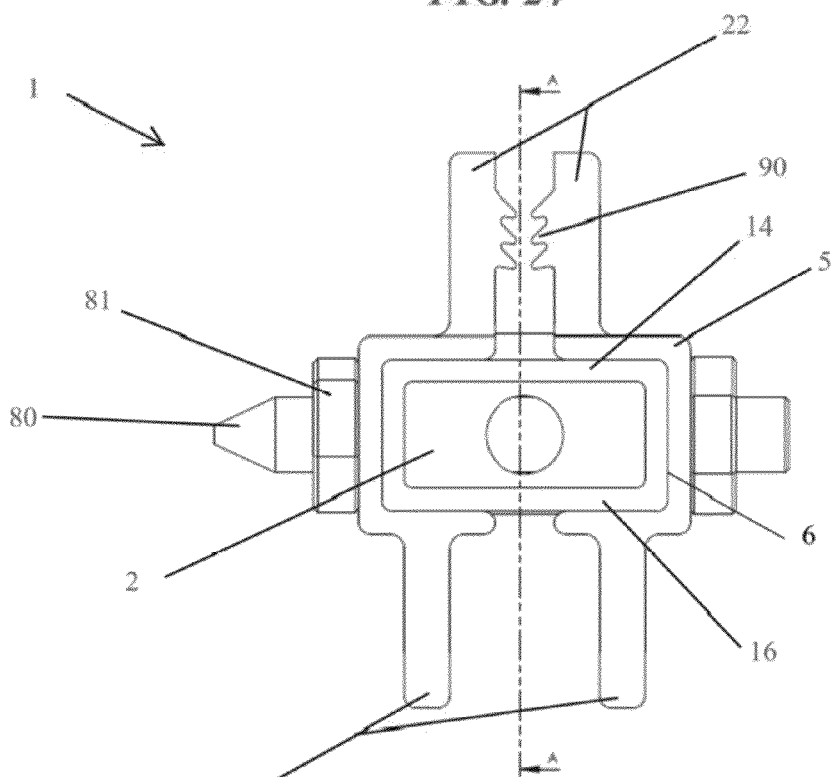
FIG. 25 is a posterior view of an interspinous process spacer according to the present invention.
Figure 26:
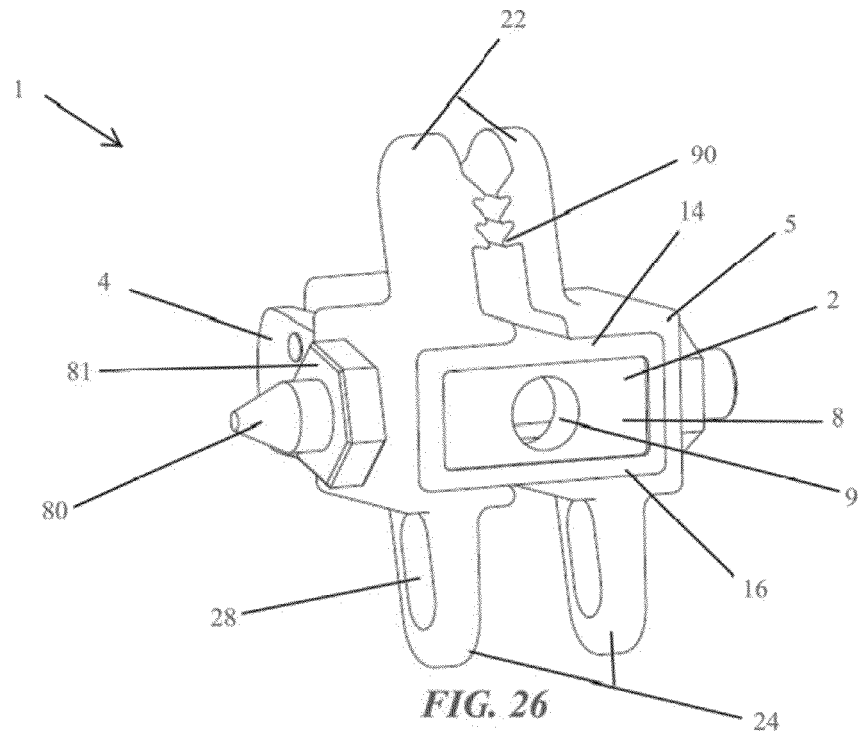
FIG. 26 is a perspective view of an interspinous process spacer according to the present invention from the rear.
Figure 27:
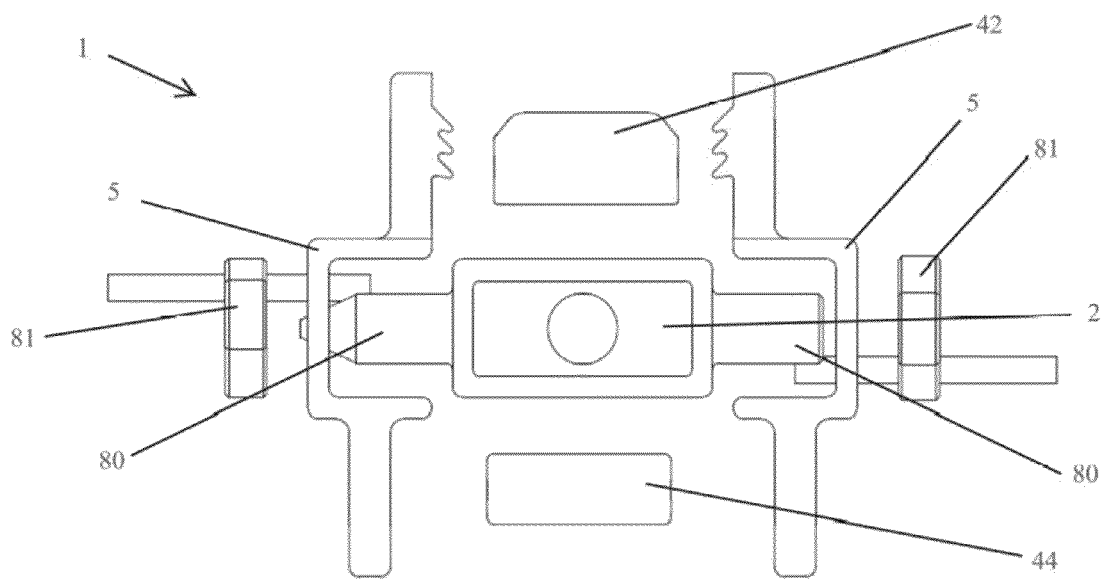
FIG. 27 is an exploded posterior view of an interspinous process spacer according to the present invention.

In a preferred embodiment, flanges 22, 24 are removable to allow for easier insertion and more flexible positioning of spacer 1 in the interbody space. FIGS. 25 and 26 show the configuration of spacer 1 wherein one or both sets of flanges 22, 24 are removable and connected to the anterior portion of main body 2 via bracket 5. Bracket 5 contains both upper 22 and lower 24 flanges on a single lateral side 4 of main body 2. Between flanges 22, 24, bracket 5 has a bump-out in which the anterior portion of main body 2 is received such that bracket 5 wraps around the anterior portion of one lateral side 4 and portions of the top 14 and bottom 16 elements of main body 2 and such that flanges 22, 24 may be positioned towards the center of the anterior portions of top and bottom elements 14, 16. The lateral side of bracket 5 is secured to the lateral side 4 of main body 2 with a screw 80 and nut 81 fastening mechanism whereby a screw 80 is inserted through corresponding holes 82 in the lateral sides of bracket 5 and main body 2 (shown in FIG. 28) and secured by nut 81. Alternatively, as shown in FIG. 27, screw 80 may be integrally formed in the main body 2 of spacer 1 such that hole 82 fits over screw 80 and nut 81 tightens down over screw 80 to secure bracket 5 to main body 2. As will be understood to one having ordinary skill in the art, the proximity of the lateral side of bracket 5 to main body 2 may be adjusted from the configuration shown in FIGS. 25 and 26, wherein bracket 5 and main body 2 are in direct contact, to a configuration wherein bracket 5 and main body 2 are spaced a desired distance apart from each other by the insertion of an additional nut, or spacer, (not shown) along the shaft of screw 80 between bracket 5 and main body 2. The width and/or number of spacers inserted between bracket 5 and main body 2 will determine the distance between these two elements so that spacer 1 can be customized to fit onto the vertebrae of an individual patient based on that patient's individual physiology and so that the "fit" of spacer 1 in the interbody space between adjacent vertebra may be precisely adjusted both during and after insertion of the spacer as will be described.

Figure 28:
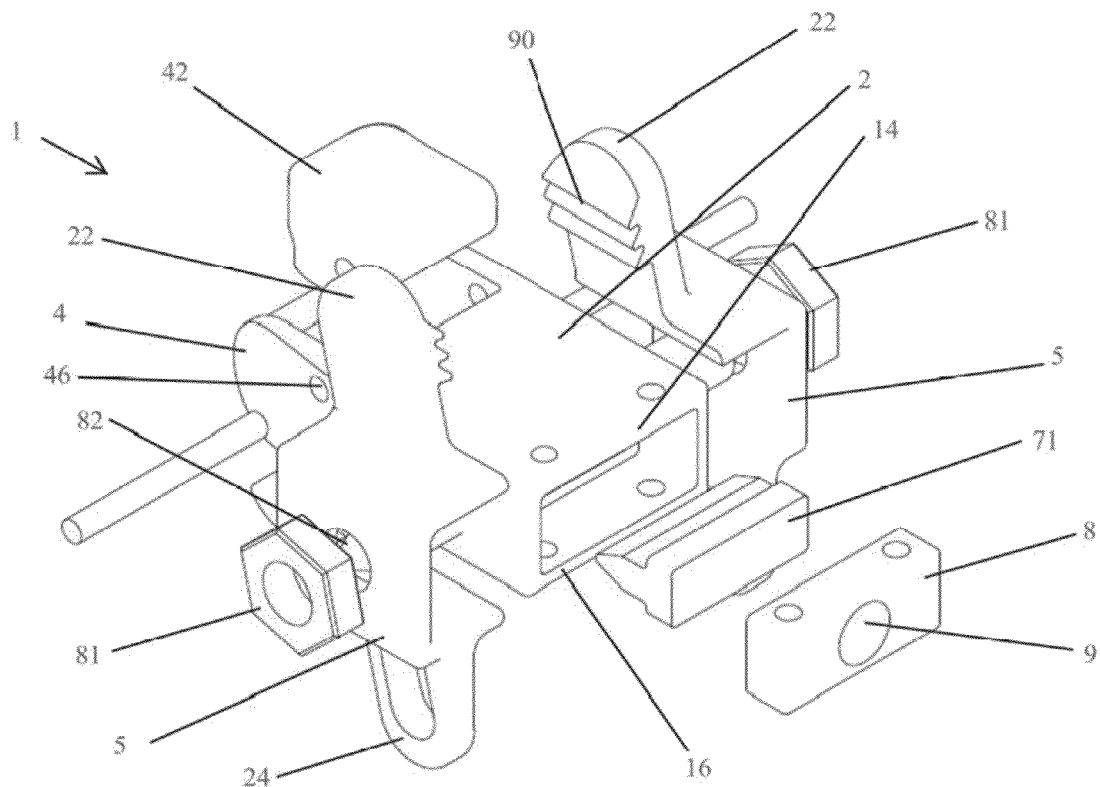
FIG. 28 is an exploded perspective view of an interspinous process spacer according to the present invention.

Additionally, and with specific reference to FIGS. 27 and 28, opposing lateral side 6 of main body 2 may also have a corresponding bracket to hold flanges 22, 24 proximate opposing lateral side 6 onto main body 2. Each bracket 5 may be secured to main body 2 by a screw and nut mechanism or by other means known in the art to permanently or adjustably fasten bracket 5 onto main body 2 during or after insertion of the main body 2 into the interbody space. As can be seen, the ability of the surgeon to remove and/or reposition one or both lateral sets of flanges 22, 24 during or after insertion of the spacer 1 into the interbody space advantageously minimizes the size of the incision through which spacer 1 may be inserted into the patient's body. In addition, as described, the distance between top and bottom pairs of flanges 22, 24 can be adjusted to meet the needs of an individual patient's physiology.

In a preferred embodiment, where one or both sets of flanges 22, 24 are removable from the main body 2 of spacer 1, upper flanges 22 additionally consist of a series of ridges 90 in place of holes 28 to assist the surgeon in accurately locating flanges 22 relative to one another upon attaching the second of the two brackets 5 (or, in the embodiment in which only one set of flanges 22, 24 is removable, upon attaching the single set of removable flanges 22, 24).

Thus, in a preferred embodiment, spacer 1, having both lateral sets of flanges 22, 24 removably secured to its main body 2, is prepared for insertion into the interbody space by removing both sets of flanges. Next, spacer 1 is implanted in a mini-open procedure in which the interspinous ligament is resected and the body portion 2 positioned within the interspinous space. As in prior preferred embodiments, the deflated expandable/collapsible member 100 is preferably secured in position prior to implantation and is most preferably inside the void 10 in a partially inflated state so as to generally fill the void and thereby be secured inside, but without actuating the operative panels 42, 44. The tapered or arcuate anterior end of the body portion 2 may provide an initial amount of distraction with direct contact to the superior (S) and inferior (I) spinous processes as it is worked into place. Alternately, an instrument may be applied to distract the vertebra and facilitate initial insertion of the spacer 1. When the main body 2 of spacer 1 is positioned to the surgeon's satisfaction, one of the two brackets 5 is positioned around the anterior portion of one lateral side 4, 6 of main body 2. Based on the preference of the surgeon, bracket 5 may first be secured to the anterior portion of main body 2 via screw 80 and nut 81, or may be first secured to the adjacent vertebra with bone screws driven through holes 28 in flanges 22, 24 such that the subsequent attachment of bracket 5 to main body 2 moves main body 2 securely into place between adjacent vertebra. Subsequently, opposing bracket 5 is attached in a similar fashion, wherein ridges 90 assist the surgeon in accurately locating the flange 22 associated with the second, opposing bracket 5 with respect to the flange 22 of the first bracket 5. In another preferred embodiment, one lateral set of flanges 22, 24 is permanently affixed to the anterior portion of one side of main body 2, or one of two brackets 5 is secured to the anterior portion of one lateral side of main body 2, prior to insertion of the spacer 1. In this latter embodiment, the surgeon need only attach one bracket 5 to the open lateral side of main body 2 after insertion of spacer 1, simplifying the process of inserting and securing spacer 1 into the interbody space and still allowing a high degree of flexibility for the surgeon to customize the shape of spacer 1 to fit into the interbody space of the individual patient. In yet another preferred embodiment, both lateral sets of flanges 22, 24 are removably mounted on brackets 5 but are secured into place on the anterior portion of main body 2 prior to insertion to allow the position of flanges 22, 24 to be adjusted only after insertion.

Figure 29:
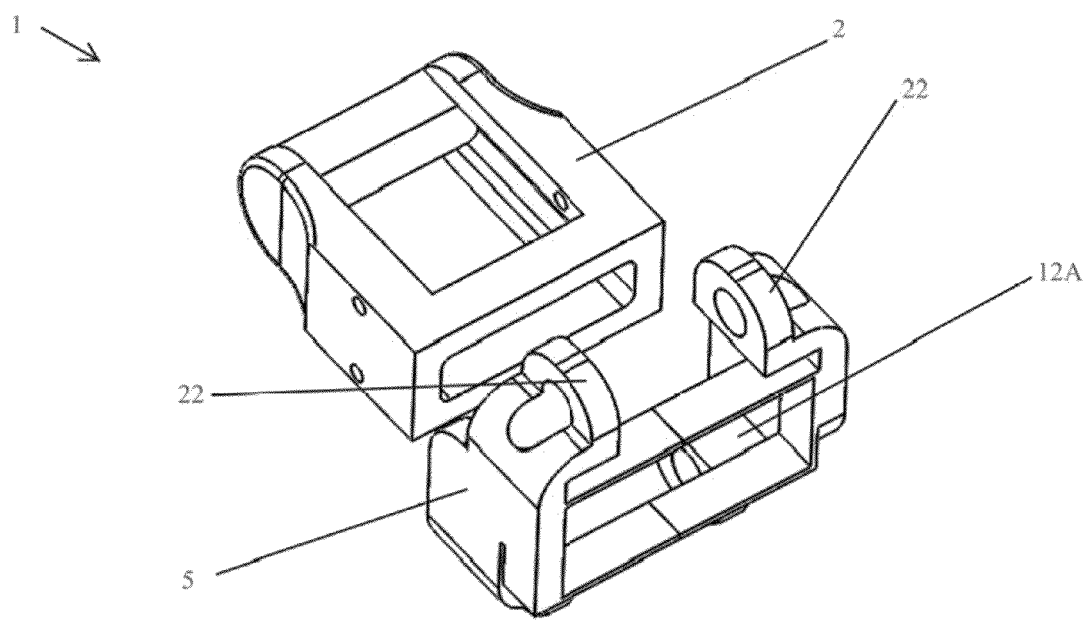
FIG. 29 is an exploded perspective view of an interspinous process spacer according to the present invention.

In yet another alternate embodiment, shown in FIG. 29, detachable bracket 5 is a unitary piece comprising both sets of flanges 22, 24 which wraps around the anterior portion of main body 2 proximate opening 12, and itself having an opening 12A corresponding to the location of opening 12 in main body 2 onto which end cap 8 may be placed. As in the previous embodiment, bracket 5 may be attached to main body 2 through a screw and nut system (not pictured). The instant configuration has the advantage of a low cross-sectional area of main body 2 for insertion into the patient's body, wherein the surgeon may accurately position the low cross-sectional profile main body 2 in the interbody space before the insertion of bracket 5. Moreover, in the instant embodiment, the surgeon may position both sets of flanges 22, 24 with respect to main body 2 and the adjacent vertebra simultaneously, which unitary bracket requires fewer steps to be attached to main body 2.

Where a single envelope expandable/collapsible member 100 is utilized the member is then expanded to an initial position to distract the vertebra by filling with a flowable material 62. Filling of the expandable/collapsible member 100 is accomplished by inserting a syringe or similar device through a port in the expandable/collapsible member, the port being accessible via the access hole 9 in the end cap 8. Filling of the expandable/collapsible member 10 causes the bulbous end 104 to enlarge which engages the ribs 51 and the inside surfaces of the panels 42, 44, forcing the operative panels 42, 44 to rotate away from the body portion so as to increase the overall height of the body portion 2 and cause the vertebra to be distracted and the intervertebral space increased. The operative panels 42, 44 bear against the proximal end of the spinous processes where they join the lamina to form the roof of the vertebral arch surrounding the vertebral foramen. In this way, the distracting force of the spacer is applied to the spinous processes at their strongest point so as to minimize the risk of fracture or damage.

The surgeon can control and moderate the amount of distraction achieved by selection of the volume of flowable material introduced into the expandable/collapsible member 100. However, maximum distraction is preferably limited by engagement of the ribs 51 with the bridging member 21 as the panels 42, 44 rotate. A maximum distraction of approximately 20 mm can be achieved by the fully inflated expandable member. In the alternate embodiment of FIG. 9, the expandable/collapsible member 100 is replaced by a mechanical spring element 109 to provide the force necessary to deploy the operative panels. Spring element 109 is be compressed and mechanically restricted to its compressed state prior to implantation, after which the mechanical restriction is removed. Selection of the spring constant prior to implantation allows the surgeon to alter the characteristics of the implant but there is limited ability to adjust this embodiment after implantation.

With respect to the embodiment of FIG. 8, subsequent to the initial implantation the volume of the expandable/collapsible member 100 can be adjusted during an in-office non-surgical procedure to add or remove fluid. Addition or subtraction of fluid is accomplished by locating the subcutaneous position of the access hole 9 and inserting a needle through the skin into the port below the whole. Increasing the volume of fluid within the envelope 16 increases the size of the end 104 of the expandable/collapsible member 100 and causes the operative panels 42, 44 to further rotate away from the body portion 2 and further distract the joint. Decreasing the volume has the opposite effect.

The flowable material 62 may be a sterile saline solution, silicone oil or gel, urethane or other viscous polymer. In certain embodiments the flowable material may be a two-part polymer such a two-part urethane such that the initial fill and distraction of the verterbral joint is accomplished by filling with a first part in flowable form. Subsequently, after the volume of the expandable/collapsible member 100 has been adjusted to a final position through the above described in-office procedure the second part of the two-part polymer may be injected by needle insertion into port 6 causing a reaction that hardens the polymer into a non-flowing elastomeric compound suitable for long term in-situ use.

In an alternate embodiment of the present invention, the operative panels 42, 44 are not fixed to the body portion 2 of the spacer 1 but rather are directly adhered or otherwise secured to the expandable/collapsible member 100. In such an embodiment the operative panels 42, 44 are seated within or on the lateral sides 4, 6 as with the previous embodiment and are maintained in position during implantation by way of their engagement with the expandable/collapsible member 100. Upon insertion the expandable/collapsible member 100 is inflated by introduction of a flowable material as described above such that the bulbous end 104 is enlarged and the operative panels 42, 44 are forced away from the base portions 2 and against the spinous processes to distract the vertebra. Operation is similar to that described in the previous embodiment except that no pin forces rotation of the operative panels 42, 44. Rather, the operative panels 42, 44 move in translation relative to the body portion 2 and can be controlled in their motion by selecting the shape of the enlarged end 104 of the expandable/collapsible member 100 prior to implantation.

Figure 13:
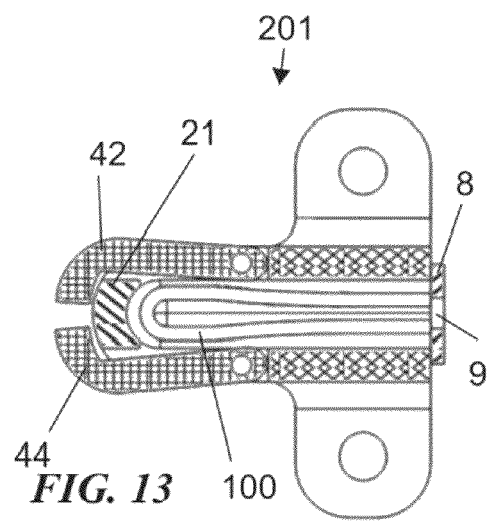
FIG. 13 is a section view of another alternate embodiment of an interspinous process spacer according to the present invention with the movable panels in a deployed position.

With reference to FIGS. 10-13, yet another alternate embodiment of the present invention is depicted in which the operative panels interspinous process spacer 201 extend anteriorly beyond the bridging member 21 and come together to enclose the bridging member within the void 10. With reference to FIG. 13, the inside surface of the bridging member 21 is adapted in this embodiment to engage the expandable/collapsible member 100 as that member is expanded so as to limit longitudinal expansion and redirect all expansion in the vertical direction for deployment of the operative panels. In this way the t-shaped expandable/collapsible member 100 previously described can be replaced with a simpler the expandable/collapsible member 100 having less structured. bulbous end region 104. Alternately, a spring mechanism such as flat spring 111 can actuate the operative panels as previously described.

Figure 14:
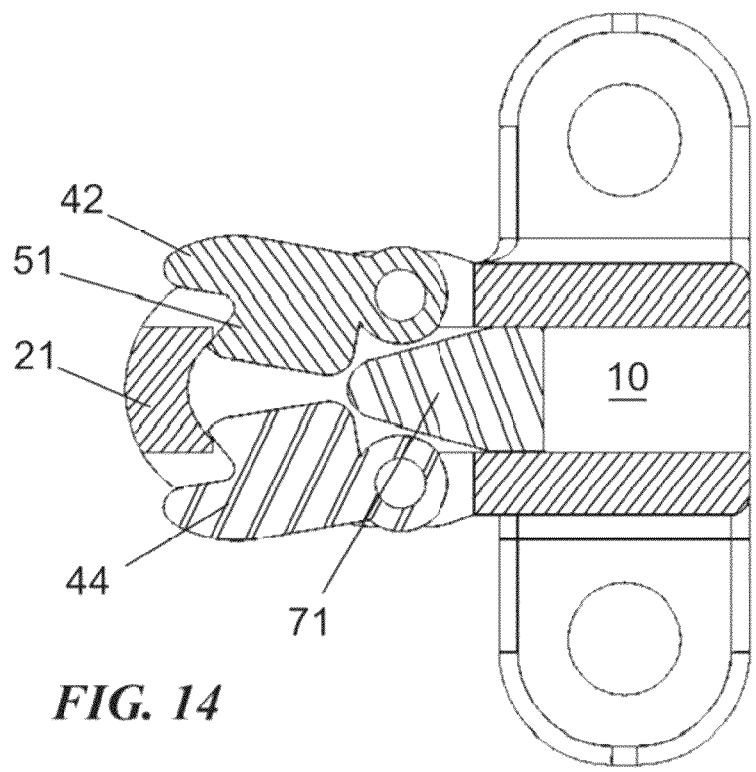
FIG. 14 is a section view of an alternate embodiment of an interspinous process spacer according to the present invention.
Figure 15:
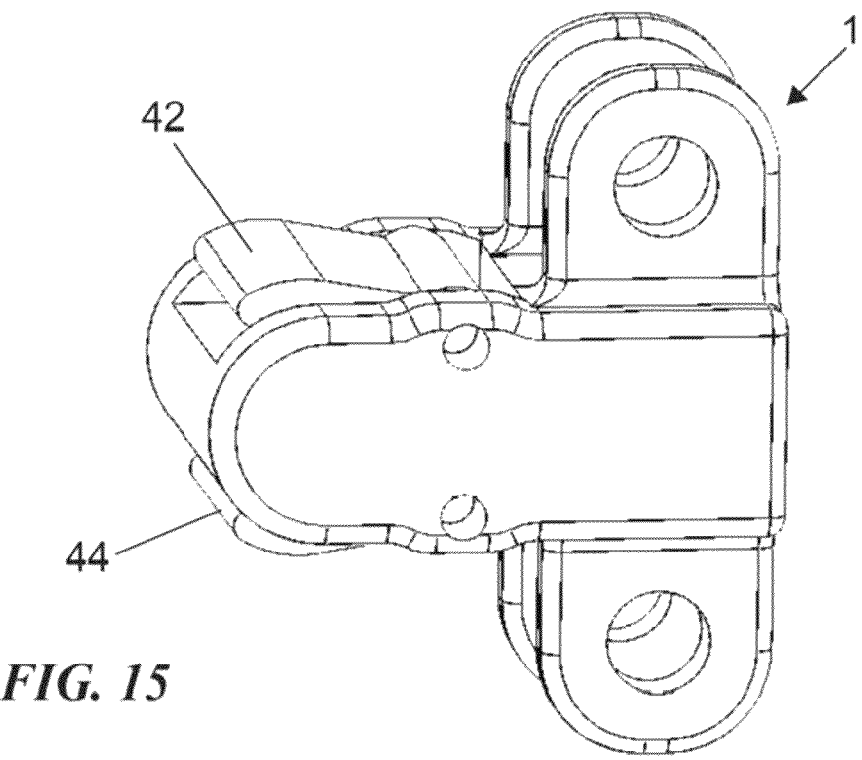
FIG. 15 is a perspective view of an alternate embodiment of an interspinous process spacer according to the present invention

With reference to FIGS. 14 and 15, yet another embodiment of the present invention is depicted in which a bumper 71 is slideably received in the void 10. The bumper 71 is preferably made of a self lubricating (i.e., low drag coefficient), hard, biocompatible polymer such as Delrin (polyoxymethylene). Bumper 71 may be cooperatively received in a track formed within the lateral sides 4, 6 or may freely float within the void 10 in which case the bumper is cooperatively sized and shaped to slide within the void without rotation and resultant binding. Bumper 71 may preferably be tapered to a distal point so as to engage the inside surface of the operative panels 42, 44 and more specifically to engage the ridges 51 so as to cause the operative panels to rotate as described above. Rotation of the operative panels 42, 44 may be limited by engagement of the ridges 51 with the bridging member 21 as also described above. The void 10 is occupied by an expandable/collapsible member (not shown) which, upon inflation, expands to cause the bumper 71 to slide horizontally (as depicted) in the void and engage the operative panels thereby causing the operative panels to pivot and increase the vertical height (again, as depicted) of the body portion 2. Translation of the horizontal motion of the bumper 71 to vertical expansion by engagement with the ridges 51 and pivoting of the operative panels 42, 44 is preferably because this arrangement permits counter rotation of the operative panels 42, 44 upon deflation of the expandable/collapsible member. Specifically, the mechanical advantage of the ridges 51 is sufficient to cause the bumper 51 to slide backward, away from the bridging member 21 when the expandable/collapsible member is collapsed as by withdrawing the flowable material/fluid.

Figure 16:
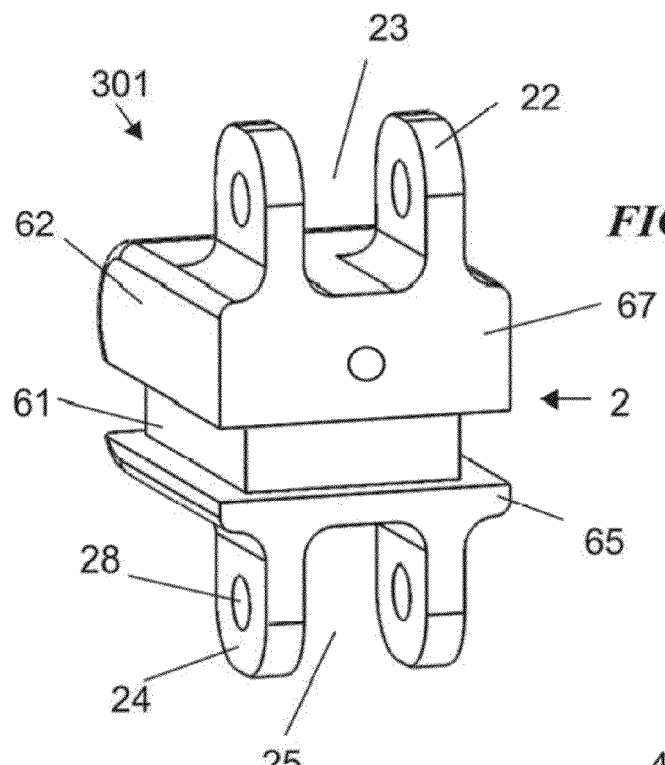
FIG. 16 is a perspective view of another alternate embodiment of an interspinous process spacer according to the present invention in a deployed position.
Figure 17:
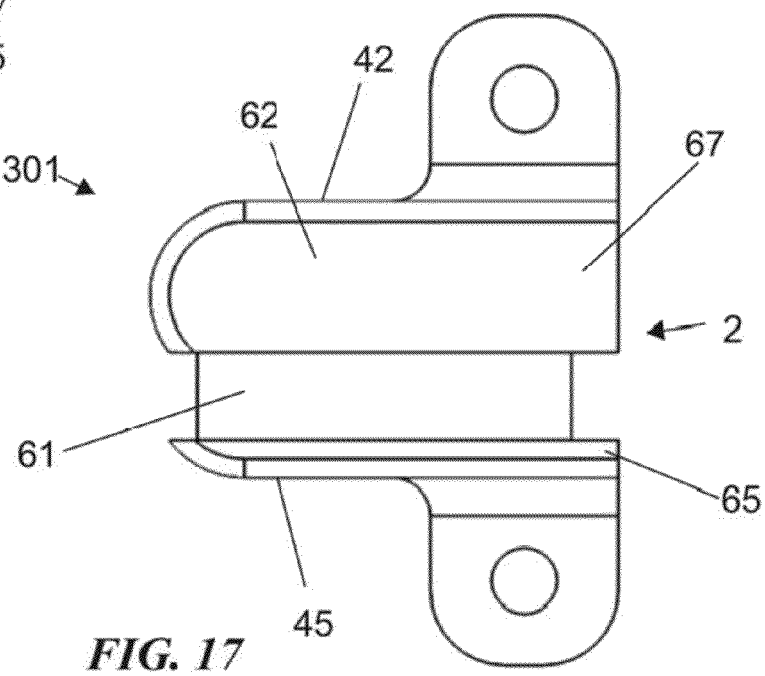
FIG. 17 is a alternate perspective view of the embodiment of FIG. 16.

With reference to FIGS. 16 and 17, yet another embodiment of the present invention is depicted in which the operative panels are fixedly attached to the body portion 2 of the interspinous process spacer 301. In this embodiment the lateral sides 4, 6 of the body portion 2 are constructed of an inner wall 61 and outer wall 62 such that the inner wall 61 is affixed to a lower portion 65 of the body portion 2 and the outer wall 62 is affixed to an upper portion 67 of the body portion 2 of the spacer 301. The inner and outer walls 61, 62 are constructed to slidingly engage with one another to enclose the inner void 10. An expandable/collapsible member (not visible) or other mechanism as described with respect to the previous embodiments is housed within the void 10 and when expanded causes the upper portion 67 and lower portion 65 to slide relative to one another and thereby increase the overall height of the device and causing the operative panels to engage the spinous process at or near their distal ends.

It should be understood that the disclosure of this may be used with a variety of interspinous process spacer forms and designs. It should also be understood that the disclosure may be constructed of a variety of suitable surgical grade materials including stainless steel and titanium as well as composite materials having suitable strength and corrosion resistance properties should such materials be approved for surgical implantation. This application is therefore intended to cover any variations, uses, or adaptations of the invention using its general principles. Further, this application is intended to cover such departures from the present disclosure as come within known or customary practice in the art to which this invention pertains.

I claim:

1. A dynamic spacer for insertion between the superior and inferior spinous processes of adjacent vertebra, comprising:
   a body portion having a first side member and a second side member and defining a void there between;
   at least one anchor member extending from said body portion for engaging said superior spinous process or said inferior spinous process when said body portion is situated between said adjacent vertebra;
   at least one operative panel moveably engaged to said first side member and said second side member; and
   an expandable member having a port for receiving fluid at a first end and having a second end proximal to said operative panel, said expandable member enlargeable upon receipt of said fluid via said port; and
   a bridging member engaged between said first side member and said second side member;
   whereby enlargement of said expandable member causes said at least one operative panel to move relative to said first and second side members thereby increasing the height of said body portion and distracting said adjacent vertebra; and
   wherein said at least one operative panel further comprises a protrusion extending from a surface thereof into said void, said protrusions adapted to engage said bridging member and thereby limit rotation of said operative panel.

2. The spacer of claim wherein said at least one anchor member comprises a first anchor member extending from said body portion for engaging said superior spinous process and a second anchor member extending from said body portion for engaging said inferior spinous process.

3. The spacer of claim 2 wherein said first anchor member comprises a first pair of flanges defining a first channel there between, said superior spinous process being received in said channel when said body portion is situated between said superior and inferior spinous processes; and wherein said second anchor member comprises a second pair of flanges defining a second channel there between, said inferior spinous process being received in said second channel when said body portion is situated between said superior and inferior spinous processes.

4. The spacer of claim 3 wherein said first pair of flanges further comprises a first hole there through for mechanically fastening said first pair of flanges to said superior spinous process, and wherein said second pair of flanges further comprises a second hole there through for mechanically fastening said second pair of flanges to said inferior spinous process.

5. The spacer of claim 4 wherein said first and second holes each comprise a slot.

6. The spacer of claim 1 wherein said at least one operative panel comprises a first operative panel forming a top surface of said body portion for engagement with said superior spinous process, and a second operative panel forming a bottom surface of said body portion for engagement with said inferior spinous process.

7. The spacer of claim 6 wherein said first operative panel and said second operative panel are each rotatably engaged between said first side member and a second side member whereby enlargement of said second end of said expandable member causes said first and second operative panels to rotate and thereby increase the height of said body portion.

8. The spacer of claim 7 further comprising a bumper slideably received within said void and engaged between said expandable member and said first and second operative panels, and wherein enlargement of said expandable member causes said bumper to slide within said void whereby said first and second operative panels are caused to rotate and thereby increase the height of said body portion.

9. The spacer of claim 8 wherein said protrusions on said first and second operative panels are further adapted to engage said bumper so as to rotate said first and second operative panels upon said sliding thereof.

10. The spacer of claim 1 wherein said at least one operative panel comprises a surface for engaging said adjacent vertebra.

11. The spacer of claim 10 wherein said surface for engaging said adjacent vertebra comprises a plurality of transverse ridges.

12. The spacer of claim 1 wherein said expandable member comprises a balloon.

13. A dynamic spacer for insertion between the superior and inferior spinous processes of adjacent vertebra, comprising:
   a body portion having a first side member and a second side member and defining a void there between, said first side member and said second side member joined by a bridging member at a first end of said body portion;
   at least one anchor member extending from said body portion for engaging said superior spinous process or said inferior spinous process when said body portion is situated between said adjacent vertebra;
   a first operative panel pivotably engaged to said first side member and said second side member to form an upper surface of said body portion, said first operative panel rotatable between a first, stowed position and a second, deployed position and having a protrusion extending therefrom into said void and adapted to engage said bridging, member when said first operative panel is fully in said deployed position;
   a second operative panel pivotably engaged to said first side member and said second side member to form a lower surface of said body portion, said second operative panel rotatable between a first, stowed position and a second, deployed position and having a protrusion extending therefrom into said void and adapted to engage said bridging member when said second operative panel is fully in said deployed position;
   an expandable member disposed within said void and having a port for receiving a fluid at a first end and having a second end proximal to said first and second operative panels, said second end adapted to be enlarged upon receipt of said fluid via said port
   whereby engagement of said enlarged second end of said expandable member causes each of said first and second operative panels to rotate from said stowed position toward said deployed position and thereby increase the height of said body portion to distract said adjacent vertebra.

14. The spacer of claim 13 wherein said expandable member comprises a balloon.

15. The spacer of claim 13 further comprising a bumper slideably disposed within said void between said expandable member and said protrusions of said first and second operative panels, whereby enlargement of said second end of said expandable member causes said bumper to slide within said void to engage said protrusions and thereby cause said first and second operative panels to rotate from said stowed position toward said deployed position.

* * * * *